United States Patent [19]

Kaneko et al.

[11] 4,310,407
[45] Jan. 12, 1982

[54] ELECTROPHORETIC APPARATUS

[75] Inventors: Nobutaka Kaneko, Hachiouji; Shinichi Kamachi, Hino, both of Japan

[73] Assignee: Olympus Optical Co., Ltd., Tokyo, Japan

[21] Appl. No.: 151,890

[22] Filed: May 21, 1980

[51] Int. Cl.³ .............. G01N 27/28; G01N 27/30; G01N 27/26
[52] U.S. Cl. .............. 204/299 R; 204/180 S; 204/180 G
[58] Field of Search .......... 204/180 S, 180 G, 299 R, 204/300 R; 424/12; 23/230 B

[56] References Cited

U.S. PATENT DOCUMENTS

| 3,421,998 | 1/1969 | Yallen | 204/299 R |
| 3,494,846 | 2/1970 | Arquembourg | 204/180 G |
| 3,764,513 | 10/1973 | Saravis | 204/180 G X |
| 3,896,021 | 7/1975 | Fosslien | 204/299 R |
| 3,932,263 | 1/1976 | Brefka | 204/180 G X |
| 4,059,501 | 11/1977 | Strickler | 204/299 R |
| 4,087,346 | 5/1978 | Kitahara | 204/299 R |
| 4,190,517 | 2/1980 | Monthony et al. | 204/299 R |

Primary Examiner—Arthur C. Prescott
Attorney, Agent, or Firm—Cushman, Darby & Cushman

[57] ABSTRACT

An electrophoretic apparatus comprising three electrode chambers serially arranged and filled with buffer solutions respectively, electrodes arranged in said electrode chambers respectively, three filter paper supports arranged above the spaces between the respective electrode chambers and above the central electrode chamber, a filter paper mounted on the central filter paper support and having both ends dipped into the buffer solution contained in the central electrode chamber and filter papers mounted on the other two filter paper supports and dipped at one end into the buffer solutions contained in the other electrode chambers. Said electrophoretic apparatus is so adapted as to form electrophoretic patterns of respective sera by electrically energizing a carrier onto which the sera are applied in two rows and which is mounted on said filter paper supports.

8 Claims, 8 Drawing Figures

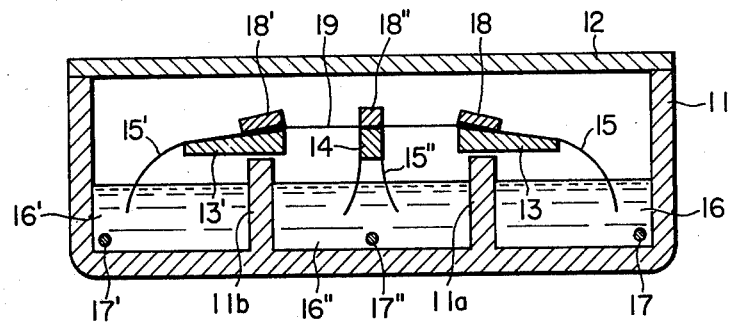
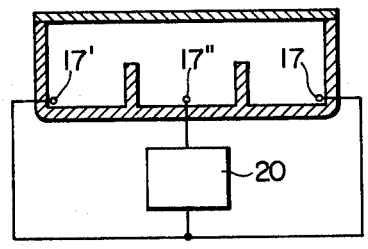
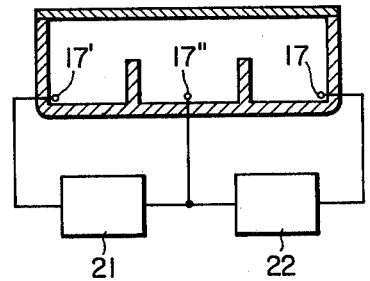
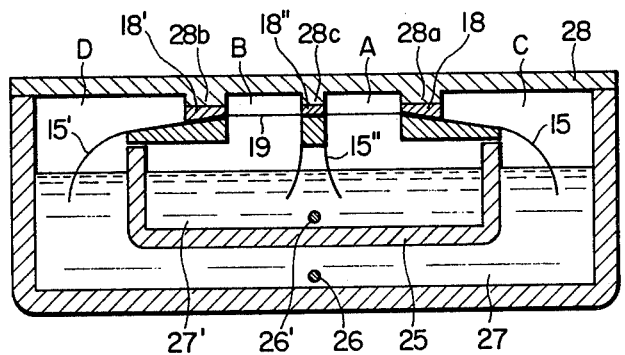

ELECTROPHORETIC APPARATUS

BACKGROUND OF THE INVENTION (a) Field of the Invention

The present invention relates to an electrophoretic apparatus, and more specifically to an electrophoretic apparatus having treating capability higher than that of the conventional apparatus.

(b) Description of the Prior Art

The electrophoresis is used for analyzing proteins contained in sera. The electrophoresis includes a step to apply serum to a carrier made of cellulose acetate film or the similar material and another step to form fractionated patterns of the serum by electrically energizing the carrier. An example of electrophoretic apparatus used in the step to form fractionated patterns is shown in FIG. 1. In this drawing, the reference numeral 1 represents the electrophoretic apparatus main body, the reference numeral 2 designates a cover, the reference numerals 3 and 3' denote filter paper supports held to the main body, for example, attached to the front and rear end faces of the main body 1 by a suitable means, the reference numerals 4 and 4' represent filter papers mounted at one end on the filter paper supports 3 and 3' respectively, the reference numeral 5 designates a carrier overlapped at both ends with the filter papers 4 and 4' and mounted on the filter paper supports 3 and 3', the reference numeral 6 and 6' denote carrier clamps, the reference numerals 7 and 7' represent electrodes, and the reference numerals 8 and 8' designate buffer solutions which are contained in the two electrode chambers separated with a partition plate 1a and in which the other ends of the filter papers 4 and 4' are dipped. In such an electrophoretic apparatus, electrical current flows from the electrode 7 to the other electrode 7' by way of the buffer solution 8, filter paper 4, carrier 5, the other filter paper 4' and the other buffer solution 8' to from fractionated patterns of a serum applied on the carrier. Such an electrophoretic apparatus requires 30 to 50 minutes for forming fractionated patterns of a serum, and such a long time required for forming fractionated patterns has constituted hindrance to enhance treating capability in electrophoresis.

In order to enhance treating capability of electrophoretic apparatus without changing the energizing time, it will be contrived to use a large number of electrophoretic apparatuses, but such solution will have a defect that it requires a large number of electrophoretic apparatuses and a wide space for installing the electrophoretic apparatuses. Though there is available another method to enhance treating capability by using an electrophoretic apparatus having larger length than that of the conventional electrophoretic apparatus, such a method requires a larger electrophoretic apparatus and is undesirable in practice. As a third method to enhace treating capability, there is contrived an electrophoretic apparatus having three electrode chambers one of which is used commonly for treating two carriers at a time. This electrophoretic apparatus is smaller than a combination of two electrophoretic apparatuses and has treating capability corresponding to two apparatuses, but is still too large for convenient practice. Furthermore, there is available a fourth method (called microzone) which permits doubling treating capability, i.e., applying double number of sera on a carrier at intervals equal to ½ of those usually selected in applying sera. However, this method does not permit convenient observation of electrophoretic patterns. For accurate photometry with a densitometer, the method requires scanning precisely at central portion of the narrow electrophoretic patterns with a minimized light spot for photometry, which in turn requires remarkable improvements in photometric optical system and electrical system.

Moreover, it is contrivable to use the electrophoretic apparatus having the construction shown in FIG. 1 in such a manner that it can treat twice the number of samples at a time by arranging samples or applying sera in two rows in the energizing direction on a carrier as shown in FIG. 2. However, this method has defects that moisture is vaporized from the carrier surface due to Joule's heat produced by energizing and that flow of buffer solution in the carrier caused by electroendosmosis as well as concentration thereof is different between the anode side and cathode side, whereby analytical result is different between samples applied on the anode side and those applied on the cathode side due to difference in electrophoretic development between both the sides.

SUMMARY OF THE INVENTION

A general object of the present invention is to provide an electrophoretic apparatus so adapted as to have enhanced treating capability and form fractionated patterns with high precision by applying samples in two rows and energizing said samples in both the rows under the same conditions.

BRIEF DESCRIPTION OF THE DRAWINGS

FIG. 3 shows a sectional view illustrating construction of an electrophoretic apparatus perferred as a first embodiment of the present invention;

FIG. 5A and FIG. 5B show diagrams illustrating wiring between the electrodes and power supply in the first embodiment of the present invention; and FIG. 6 shows a sectional view illustrating the construction of a second embodiment of the present invention.

DETAILED DESCRIPTION OF THE PREFERRED EMBODIMENTS

Figure 1:
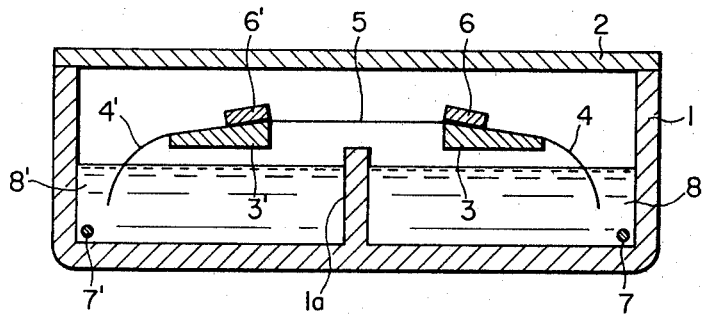
FIG. 1 shows a sectional view illustrating the construction of the conventional electrophoretic apparatus.
Figure 2:
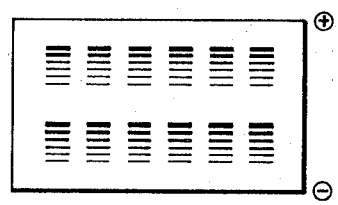
FIG. 2 shows a diagram schematically illustrating electrophoretic patterns obtained by electrophoresis carried out by the conventional method to apply samples in two rows on a carrier.

Now, the present invention will be described more detailedly with reference to the embodiments illustrated in the accompanying drawings. A first embodiment of the electrophoretic apparatus according to the present invention is illustrated in FIG. 3 in which the reference numeral 11 represents an electrophoretic apparatus main body divided by partitions 11a and 11b into three electrode chambers filled with buffer solutions 16, 16' and 16" respectively. The reference numeral 12 designates a cover, the reference numerals 13 and 13' denote filter paper supports, the reference numeral 14 represents another filter paper support arranged between the filter paper supports 13 and 13', the reference numerals 15 and 15' designate filter papers mounted at one end on the filter paper supports 13 and 13' and dipped at the other end into the buffer solutions 16 and 16', the reference numeral 15" denotes a filter paper mounted at central portion thereof on the filter paper support 14 and dipped at both ends thereof into the buffer solution 16", the reference numerals 17, 17' and 17" represent electrodes, and the reference numerals 18 and 18' designate carrier clamps.

Figure 4A:
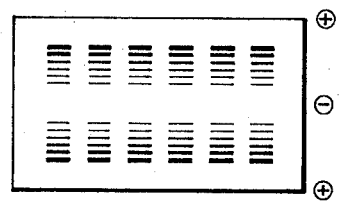
FIG. 4A and FIG. 4B shows diagrams schematically illustrating electrophoretic patterns obtained with the electrophoretic apparatus according to the present invention.
Figure 4B:
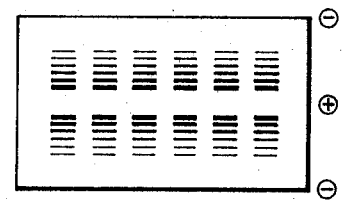

In order to obtain electrophoretic patterns with the electrophoretic apparatus illustrated as the first embodiment, a carrier 19 on which sera are applied in two rows is placed the position shown in the drawing. Speaking concretely, the carrier 19 is placed in such a position that the central portion between the sera applied in two rows is brought into contact with the filter paper 15" which is mounted on the filter paper support 14. The sera are electrically energized after the carrier is placed as described above. That is to say, filter paper 15, carrier 19, filter paper 15" and electrode 17" are energized from the electrode 17, whereas the filter paper 15', carrier 19, filter paper 15" and electrode 17" are energized from the electrode 17' to form electrophoretic patterns of the samples applied in the two rows respectively as shown in FIG. 4A and FIG. 4B.

FIG. 5A and FIG. 5B show examples of wiring between the respective electrodes and DC power supplies in the electrophoretic apparatus preferred as the first embodiment. FIG. 5A illustrates a case where a single power supply 20 is used, and electrodes 17 and 17' are kept at the same potential since they are connected to each other. FIG. 5B shows another case where two power supplies 21 and 22 are employed.

FIG. 6 shows a second embodiment of the present invention using two electrodes. In this embodiment, the electrophoretic apparatus comprises a partition plate having a shape different from that of the partition plates adopted in the first embodiment. Speaking concretely, the partition plate 25 used in the second embodiment has an U-shape and is fixed to the front and rear end faces of the main body by a suitable attaching means so as to separate the electrode chamber into a section inside the partition plate 25 and another section outside said plate. In these two sections in the electrode chamber, electrodes 26 and 26' are arranged and buffer solutions 27 and 27' are filled. The other structural details remain substantially unchanged from those in the first embodiment illustrated in FIG. 3. Owing to such a construction of the second embodiment, the filter paper 15, carrier 19, filter paper 15" and electrode 26' are energized from the electrode 26, whereas the filter paper 15', carrier 19, filter paper 15" and electrode 26' are energized from the electrode 26. In the second embodiment, the carrier is electrically energized in the manner similar to that in the first embodiment so as to form electrophoretic patterns as shown in FIG. 4A and FIG. 4B.

On the lower surface of the cover 28 of the electrophoretic apparatus shown in FIG. 6, there are formed protrusions 28a, 28b and 28c at the positions corresponding to the carrier clamps 18, 18' and 18" respectively. Owing to these protrusions formed on the cover, the spaces A and B located above the carrier 19 are sealed from the other spaces C and D when the cover is closed to bring the protrusions 28a, 28b and 28c into close contact with the carrier clamps 18, 18' and 18" respectively. Therefore, when heat is generated through electrical energizing and buffer solutions are vaporized, convection does not take place between the spaces A, B kept at relatively high humidity and the spaces C, D kept at relatively low humidity, thereby maintaining the former spaces at constant high humidities respectively to assure nearly equal electrophoretic conditions in both the spaces. In an electrophoretic apparatus, energizing direction is reversed for every two analyses for avoiding adverse effect on electrophoretic patterns due to difference in pH level between the buffer solutions in the respective electrode chambers. When electrophoretic conditions are the same between the spaces A and B as described above, no difference can be produced on the electrophoretic patterns by reversing the energizing direction. On the cover shown in FIG. 6, the carrier clamps 18, 18' and 18" may be bonded or attached by a suitable means to the protrusions 28a, 28b and 28c so as to make the cover servable also as the carrier clamps. A cover having such protrusions is usable also in the first embodiment of the present invention.

In the two embodiments described above, the filter papers used for supplying the buffer solutions and electric current may be replaced with equivalent members made of a foamed material such as sponge. Further, it is possible to use, in place of the filter paper 15" and filter paper support 18"', a trapezoidal member which is made of a foamed materials and servable as both the filter paper and filter paper support at a time. Furthermore, it is possible to design the filter paper 15 and filter paper support 13 as an integral member made of a foamed material and arrange it so as to dip its low end into the buffer solution 8. The filter paper 15' and filter paper support 13' can be designed and arranged in quite the similar manner.

As is understood from the foregoing detailed descriptions, the electrophoretic apparatus according to the present invention comprises the members for supplying buffer solutions and electric current arranged at the position to be brought into contact with the central portion of the carrier, permits forming electrophoretic patterns by electrically energizing samples applied in two rows on a carrier, and is capable to treating samples in a number twice as large as that treatable with the conventional electrophoretic apparatus. Further, the electrophoretic apparatus according to the present invention electrically energizes the samples in a direction symmetrical with regard to the right and left sample rows, and permits obtaining electrophoretic patterns developed similarly in both the sample rows. Moreover, the electrophoretic apparatus according to the present invention can be designed relatively compact though it is a little enlarged since it requires a carrier a little wider than conventional. The second embodiment of the present invention uses only two electrodes one of which is equivalent to two electrodes usually arranged at both the sides. A single electrode used commonly as described above assures the same energizing condition for the samples applied in two rows and makes it possible to obtain electrophoretic patterns developed similarly in both the right and left rows.

We claim:

1. An electrophoretic apparatus comprising at least two electrode chambers filled with buffer solutions respectively, electrodes arranged in said electrode chambers respectively, three filter paper supports, and three members for supplying said buffer solutions and electric current which are mounted on said filter paper supports respectively and dipped at one end into the buffer solutions contained in said electrode chambers, and so adapted as to form electrophoretic patterns by electrically energizing a carrier on which sera are applied in two rows after placing said carrier on said members for supplying the buffer solutions and electric current in such a manner that the portions of the carrier free from the sera are brought into contact with said members.

2. An electrophoretic apparatus according to claim 1 wherein said electrode chambers are formed in a number of three, the one of said three members for supplying the buffer solutions and electric current which is arranged on the central filter paper support is dipped at both ends thereof into the buffer solutions contained in the central electrode chamber, and the other two members are dipped at one end thereof into the buffer solutions contained in the electrode chambers located on both sides respectively.

3. An electrophoretic apparatus according to claim 1 wherein said electrode chambers are formed as two outside and inside electrode chambers, the one of said three members for supplying the buffer solutions and electric current which is mounted on the central one of said three filter paper supports is dipped at both ends thereof into the buffer solution contained in said inside electrode chamber, and other two members are dipped at one end thereof into the buffer solution contained in said outside electrode chamber.

4. An electrophoretic apparatus according to claim 1 additionally comprising carrier clamps to be placed on said filter paper supports respectively.

5. An electrophoretic apparatus according to claim 4 comprising a cover having protrusions to be brought into contact with said carrier clamps respectively.

6. An electrophoretic apparatus according to claim 5 wherein said carrier clamps are formed integrally with said cover.

7. An electrophoretic apparatus according to claim 1 wherein said members for supplying the buffer solution and electric current are filter papers.

8. An electrophoretic apparatus according to claim 1 wherein the central one of said three filter paper supports is made of a foamed material (porous material) and serves also as the member for supplying buffer solution and electric current which is mounted on the central filter paper support.

* * * * *